United States Patent
Kramer

(12) United States Patent Kramer
(10) Patent No.: US 6,450,987 B1
(45) Date of Patent: Sep. 17, 2002

(54) COLLAPSIBLE GUIDEWIRE LUMEN

(75) Inventor: Hans W. Kramer, Temecula, CA (US)

(73) Assignee: Innercool Therapies, Inc., San Diego, CA (US)

( * ) Notice: Subject to any disclaimer, the term of this patent is extended or adjusted under 35 U.S.C. 154(b) by 30 days.

(21) Appl. No.: 09/775,708

(22) Filed: Feb. 1, 2001

(51) Int. Cl.⁷ ............................................. A61M 5/00
(52) U.S. Cl. ............................................. 604/43; 604/523
(58) Field of Search .................................... 604/43, 523

(56) References Cited

U.S. PATENT DOCUMENTS

| | | |
|---|---|---|
| 4,762,129 A | 8/1988 | Bonzel |
| 4,820,349 A | 4/1989 | Saab |
| 5,002,531 A | 3/1991 | Bonzel |
| 5,106,368 A * | 4/1992 | Uldall et al. .............. 604/43 |
| 5,306,261 A | 4/1994 | Alliger et al. |
| 5,443,456 A | 8/1995 | Alliger et al. |
| 5,486,208 A | 1/1996 | Ginsburg |
| 5,588,438 A | 12/1996 | McKown et al. |
| 5,643,197 A | 7/1997 | Brucker et al. |
| 5,735,809 A | 4/1998 | Gorsuch |
| 5,837,003 A | 11/1998 | Ginsburg |
| 5,861,021 A | 1/1999 | Thome et al. |
| 5,879,329 A | 3/1999 | Ginsburg |
| 5,913,885 A | 6/1999 | Klatz et al. |
| 5,957,963 A | 9/1999 | Dobak, III |
| 5,968,009 A * | 10/1999 | Siman .................... 604/43 |
| 5,989,238 A | 11/1999 | Ginsburg |
| 6,019,783 A | 1/2000 | Philips et al. |
| 6,033,383 A | 3/2000 | Ginsburg |
| 6,042,559 A | 3/2000 | Dobak, III |
| 6,051,019 A | 4/2000 | Dobak, III |
| 6,096,068 A | 8/2000 | Dobak, III et al. |
| 6,110,168 A | 8/2000 | Ginsburg |
| 6,126,684 A | 10/2000 | Gobin et al. |
| 6,146,411 A | 11/2000 | Noda et al. |
| 6,149,670 A | 11/2000 | Worthen et al. |
| 6,149,673 A | 11/2000 | Ginsburg |
| 6,149,676 A | 11/2000 | Ginsburg |
| 6,149,677 A | 11/2000 | Dobak, III |
| 6,165,207 A | 12/2000 | Balding et al. |

FOREIGN PATENT DOCUMENTS

| | | |
|---|---|---|
| WO | WO 94/16760 | 8/1994 |
| WO | WO 97/25011 | 7/1997 |
| WO | WO 98/26831 | 6/1998 |
| WO | WO 98/31312 | 7/1998 |
| WO | WO 99/37226 | 7/1999 |
| WO | WO 99/48449 | 9/1999 |
| WO | WO 99/66970 | 12/1999 |
| WO | WO 99/66971 | 12/1999 |
| WO | WO 00/09054 | 2/2000 |
| WO | WO 00/10494 | 3/2000 |
| WO | WO 00/38601 | 7/2000 |
| WO | WO 00/47145 | 8/2000 |
| WO | WO 00/48670 | 8/2000 |
| WO | WO 00/51534 | 9/2000 |
| WO | WO 00/53135 | 9/2000 |
| WO | WO 00/57823 | 10/2000 |
| WO | WO 00/62837 | 10/2000 |
| WO | WO 00/66053 | 11/2000 |
| WO | WO 00/72779 | 12/2000 |
| WO | WO 00/72787 | 12/2000 |
| WO | WO 01/03606 | 1/2001 |
| WO | WO 01/08580 | 2/2001 |
| WO | WO 01/10323 | 2/2001 |

\* cited by examiner

*Primary Examiner*—Philippe Derakshani
(74) *Attorney, Agent, or Firm*—Gerald W. Spinks

(57) ABSTRACT

A wire guided fluid catheter assembly having a collapsible guidewire lumen. Pressurization of a fluid lumen in the catheter assembly collapses the guidewire lumen, thereby increasing the fluid flow capacity of the catheter assembly.

14 Claims, 1 Drawing Sheet

COLLAPSIBLE GUIDEWIRE LUMEN

CROSS REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of the Invention

This invention is in the field of wire guided fluid catheter assemblies.

2. Background Art

In conventional wire guided fluid catheter assemblies intended for insertion into a vascular system of a patient, such as into blood vessels, the tubular catheter body has at least one lumen provided for the passage of a guidewire. This guidewire lumen usually passes either through the main lumen of the catheter or along the outer surface of the main catheter body. Where the guidewire lumen passes through the main lumen of the catheter, the guidewire lumen occupies space within the catheter body that would otherwise be available for the flow of fluid, thereby reducing the fluid flow capacity of a given diameter catheter body. Put differently, a catheter assembly having a given fluid flow capacity must have a larger diameter catheter body, because of the presence of the guidewire lumen.

Similarly, where the guidewire lumen is positioned along the outer surface of the main catheter body, the presence of the guidewire lumen reduces the space available for the fluid lumen, in a catheter assembly having a given overall diameter. Said differently, the outer diameter of a catheter assembly having a given fluid flow capacity is increased by the presence of the guidewire lumen on the outer surface of the catheter body.

In either case, either the fluid flow capacity of the catheter assembly is reduced, or the minimum size blood vessel in which the catheter assembly can be used is increased, thereby limiting its usefulness.

It would be beneficial to have a catheter assembly in which the guidewire lumen does not reduce or limit the available space for the fluid lumen, and which does not add to the overall diameter of the catheter assembly. Such an assembly would maximize the fluid flow capacity of a catheter sized for insertion into any given size blood vessel.

BRIEF SUMMARY OF THE INVENTION

The present invention is a wire guided catheter assembly in which the guidewire lumen is adapted to collapse upon pressurization of the fluid lumen, thereby maximizing the size of the flow path available for fluid flow. The guidewire lumen is formed within the main catheter body, and within the fluid flow lumen. The entire catheter body can be used as a fluid flow lumen, or a separate fluid flow lumen may be established within a portion of the catheter body. In either case, the guidewire lumen is within the fluid flow lumen. In its expanded state, the guidewire lumen occupies a significant portion of the fluid flow lumen. In its collapsed state, the guidewire lumen occupies a very insignificant portion, or almost none, of the fluid flow lumen.

The novel features of this invention, as well as the invention itself, will be best understood from the attached drawings, taken along with the following description, in which similar reference characters refer to similar parts, and in which:

DETAILED DESCRIPTION OF THE INVENTION

Figure 1:
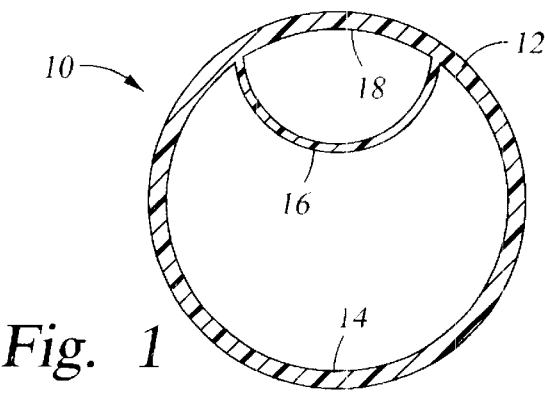
FIG. 1 is a transverse section view of a first embodiment of a catheter assembly according to the present invention, with the guidewire lumen attached to the inside of the main body of the catheter.

As seen in FIG. 1, the first embodiment of the catheter assembly 10 according to the present invention has a main catheter body 12, which encompasses a fluid flow lumen 14. Further, the main catheter body 12 encompasses a guidewire lumen 18, which is formed in part by a guidewire lumen wall 16 and in part by a portion of the main catheter body 12. The guidewire lumen wall 16 is constructed of a relatively flexible material, and with a relatively thin wall thickness, preferably for example in the range of 0.0015 inch to 0.0020 inch. The guidewire lumen wall 16 is shown fully distended, resulting in the guidewire lumen 18 being in its expanded state. In this condition, the guidewire lumen 18 is best suited for the passage of a guidewire (not shown), facilitating the insertion of the catheter assembly 10 through a vascular system of a patient. It can be seen that, when the guidewire lumen 18 is in its expanded state, the guidewire lumen 18 occupies a significant portion of the cross sectional area of the catheter body 12, thereby significantly reducing the cross sectional area which would be available for the fluid flow lumen 14. Therefore, for a given diameter of the catheter body 12, the available fluid flow capacity through the fluid flow lumen 14 is significantly limited by the expansion of the guidewire lumen 18.

Figure 2:
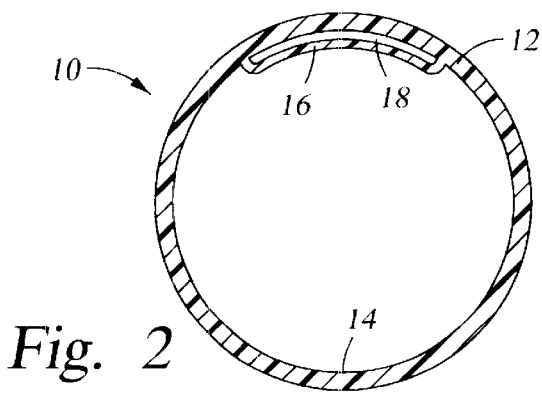
FIG. 2 is a transverse section view of the embodiment shown in FIG. 1, with the guidewire lumen in its collapsed state.

Once the catheter assembly 10 has been inserted to a desired point in the vascular system of the patient, the fluid flow lumen 14 can be pressurized with fluid, to a pressure sufficient to cause the guidewire lumen wall 16 to flex or move toward the guidewire lumen 18, thereby collapsing the guidewire lumen 18 as shown in FIG. 2. The pressure necessary for causing the collapse of the guidewire lumen 18 may be approximately 30 psig. The guidewire can be removed from the guidewire lumen 18 before pressurization of the fluid flow lumen 14, thereby allowing the guidewire lumen 18 to fully collapse. It can be seen that, with the guidewire lumen 18 collapsed, the cross sectional area of the catheter body 12 available for the fluid flow lumen 14 has significantly increased, essentially maximizing the fluid flow capacity of the catheter assembly 10 for a given overall diameter. When it is desired to again insert the guidewire into the guidewire lumen 18, the guidewire lumen 18 can be returned to its expanded state, shown in FIG. 1, by pressurizing the guidewire lumen 18 with a fluid such as a saline solution.

Figure 3:
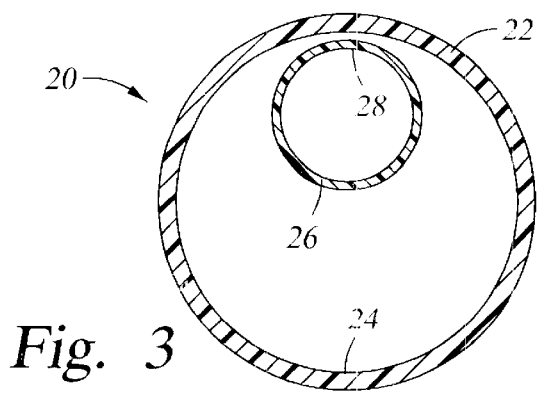
FIG. 3 is a transverse section view of a second embodiment of a catheter assembly according to the present invention, with the guidewire lumen separately formed within the main body of the catheter.

As seen in FIG. 3, a second embodiment of the catheter assembly 20 according to the present invention has a main catheter body 22, which encompasses a fluid flow lumen 24. Further, the main catheter body 22 encompasses a guidewire lumen 28, which is formed entirely by a tubular guidewire passageway 26 separately formed within the fluid flow lumen 24 of the main catheter body 22. The tubular guidewire passageway 26 is constructed of a relatively flexible material, and with a relatively thin wall thickness, preferably for example in the range of 0.0015 inch to 0.0020 inch. The tubular guidewire passageway 26 is shown fully distended, resulting in the guidewire lumen 28 being in its expanded state. In this condition, the guidewire lumen 28 is best suited for the passage of a guidewire (not shown), facilitating the insertion of the catheter assembly 20 through a vascular system of a patient. It can be seen that, when the guidewire lumen 28 is in its expanded state, the guidewire lumen 28 occupies a significant portion of the cross sectional area of the catheter body 22, thereby significantly reducing the cross sectional area which would be available for the fluid flow lumen 24. Therefore, for a given diameter of the catheter body 22, the available fluid flow capacity through the fluid flow lumen 24 is significantly limited by the expansion of the guidewire lumen 28.

Figure 4:
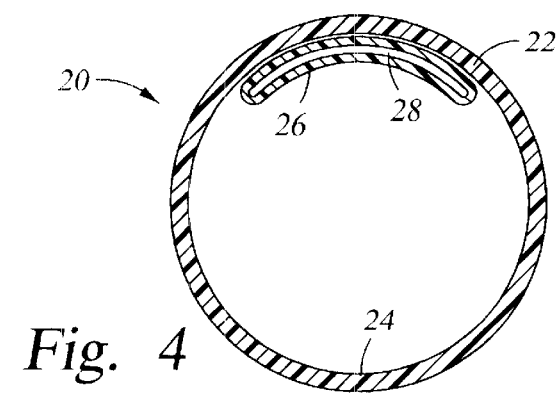
FIG. 4 is a transverse section view of the embodiment shown in FIG. 3, with the guidewire lumen in its collapsed state.

Once the catheter assembly 20 has been inserted to a desired point in the vascular system of the patient, the fluid flow lumen 24 can be pressurized with fluid, to a pressure sufficient to cause the tubular guidewire passageway 26 to flex or move into the guidewire lumen 28, thereby collapsing the guidewire lumen 28 as shown in FIG. 4. The pressure necessary for causing the collapse of the guidewire lumen 28 may be approximately 30 psig. The guidewire can be removed from the guidewire lumen 28 before pressurization of the fluid flow lumen 24, thereby allowing the guidewire lumen 28 to fully collapse. It can be seen that, with the guidewire lumen 28 collapsed, the cross sectional area of the catheter body 22 available for the fluid flow lumen 24 has significantly increased, essentially maximizing the fluid flow capacity of the catheter assembly 20 for a given overall diameter. When it is desired to again insert the guidewire into the guidewire lumen 28, the guidewire lumen 28 can be returned to its expanded state, shown in FIG. 3, by pressurizing the guidewire lumen 28 with a fluid.

Figure 5:
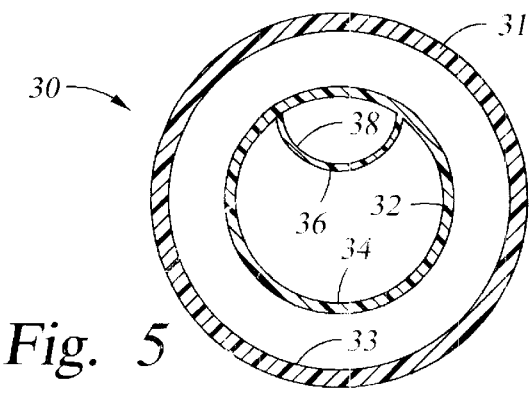
FIG. 5 is a transverse section view of a third embodiment of a catheter assembly according to the present invention, with the fluid lumen separately formed within the main body of the catheter, and the guidewire lumen attached to the inside of the fluid lumen.

As seen in FIG. 5, a third embodiment of the catheter assembly 30 according to the present invention has a main catheter body 31, which encompasses a main catheter lumen 33. The main catheter lumen 33 can be utilized for the return of fluid through the catheter assembly 30, or for any other purpose. The main catheter body 31 also encompasses a fluid flow lumen 34, which is formed by a separate tubular fluid flow passageway 32 within the main catheter lumen 33. Further, the main catheter body 31 and the tubular fluid flow passageway 32 both encompass a guidewire lumen 38, which is formed in part by a guidewire lumen wall 36 and in part by a portion of the tubular fluid flow passageway 32. The guidewire lumen wall 36 is constructed of a relatively flexible material, and with a relatively thin wall thickness, preferably for example in the range of 0.0015 inch to 0.0020 inch. The guidewire lumen wall 36 is shown fully distended, resulting in the guidewire lumen 38 being in its expanded state. In this condition, the guidewire lumen 38 is best suited for the passage of a guidewire (not shown), facilitating the insertion of the catheter assembly 30 through a vascular system of a patient. It can be seen that, when the guidewire lumen 38 is in its expanded state, the guidewire lumen 38 occupies a significant portion of the cross sectional area of the tubular fluid flow passageway 32, thereby significantly reducing the cross sectional area which would be available for the fluid flow lumen 34. Therefore, for a given diameter of the catheter body 31, and for a given diameter of the tubular fluid flow passageway 32, the available fluid flow capacity through the fluid flow lumen 34 is significantly limited by the expansion of the guidewire lumen 38.

Figure 6:
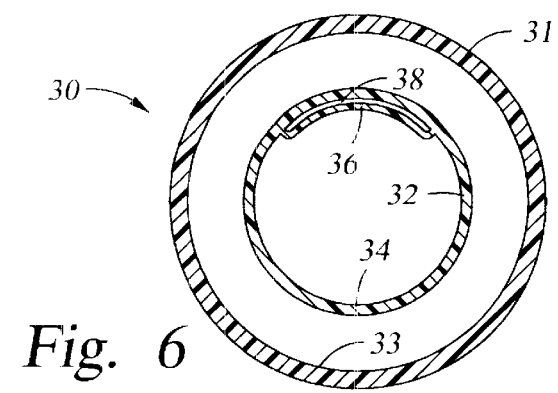
FIG. 6 is a transverse section view of the embodiment shown in FIG. 5, with the guidewire lumen in its collapsed state.

Once the catheter assembly 30 has been inserted to a desired point in the vascular system of the patient, the fluid flow lumen 34 can be pressurized with fluid, to a pressure sufficient to cause the guidewire lumen wall 36 to flex or move toward the guidewire lumen 38, thereby collapsing the guidewire lumen 38 as shown in FIG. 6. The pressure necessary for causing the collapse of the guidewire lumen 38 may be approximately 30psig. The guidewire can be removed from the guidewire lumen 38 before pressurization of the fluid flow lumen 34, thereby allowing the guidewire lumen 38 to fully collapse. It can be seen that, with the guidewire lumen 38 collapsed, the cross sectional area of the tubular fluid flow passageway 32 available for the fluid flow lumen 34 has significantly increased, essentially maximizing the fluid flow capacity of the catheter assembly 30 for a given overall diameter. When it is desired to again insert the guidewire into the guidewire lumen 38, the guidewire lumen 38 can be returned to its expanded state, shown in FIG. 5, by pressurizing the guidewire lumen 38 with a fluid such as a saline solution.

Figure 7:
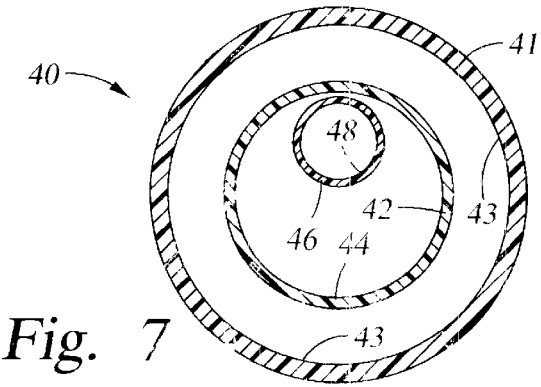
FIG. 7 is a transverse section view of a fourth embodiment of a catheter assembly according to the present invention, with the fluid lumen separately formed within the main body of the catheter, and the guidewire lumen separately formed within the fluid lumen.

As seen in FIG. 7, a fourth embodiment of the catheter assembly 40 according to the present invention has a main catheter body 41, which encompasses a main catheter lumen 43. The main catheter lumen 43 can be utilized for the return of fluid through the catheter assembly 40, or for any other purpose. The main catheter body 41 also encompasses a fluid flow lumen 44, which is formed by a separate tubular fluid flow passageway 42 within the main catheter lumen 43. Further, the main catheter body 41 and the tubular fluid flow passageway 42 both encompass a guidewire lumen 48, which is formed entirely by a tubular guidewire passageway 46 separately formed within the fluid flow lumen 44 of the tubular fluid flow passageway 42. The tubular guidewire passageway 46 is constructed of a relatively flexible material, and with a relatively thin wall thickness, preferably for example in the range of 0.0015 inch to 0.0020 inch. The tubular guidewire passageway 46 is shown fully distended, resulting in the guidewire lumen 48 being in its expanded state. In this condition, the guidewire lumen 48 is best suited for the passage of a guidewire (not shown), facilitating the insertion of the catheter assembly 40 through a vascular system of a patient. It can be seen that, when the guidewire lumen 48 is in its expanded state, the guidewire lumen 48 occupies a significant portion of the cross sectional area of the tubular fluid flow passageway 42, thereby significantly reducing the cross sectional area which would be available for the fluid flow lumen 44. Therefore, for a given diameter of the catheter body 41, and for a given diameter of the tubular fluid flow passageway 42, the available fluid flow capacity through the fluid flow lumen 44 is significantly limited by the expansion of the guidewire lumen 48.

Figure 8:
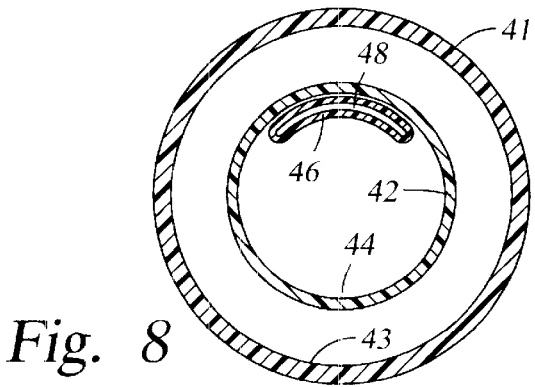
FIG. 8 is a transverse section view of the embodiment shown in FIG. 7, with the guidewire lumen in its collapsed state.

Once the catheter assembly 40 has been inserted to a desired point in the vascular system of the patient, the fluid flow lumen 44 can be pressurized with fluid, to a pressure sufficient to cause the tubular guidewire passageway 46 to flex or move into the guidewire lumen 48, thereby collapsing the guidewire lumen 48 as shown in FIG. 8. The pressure necessary for causing the collapse of the guidewire lumen 48 may be approximately 30 psig. The guidewire can be removed from the guidewire lumen 48 before pressurization of the fluid flow lumen 44, thereby allowing the guidewire lumen 48 to fully collapse. It can be seen that, with the guidewire lumen 48 collapsed, the cross sectional area of the tubular fluid flow passageway 42 available for the fluid flow lumen 44 has significantly increased, essentially maximizing the fluid flow capacity of the catheter assembly 40 for a given overall diameter. When it is desired to again insert the guidewire into the guidewire lumen 48, the guidewire lumen 48 can be returned to its expanded state, shown in FIG. 7, by pressurizing the guidewire lumen 48 with a fluid.

While the invention as herein shown and disclosed is fully capable of providing the advantages hereinbefore stated, it is to be understood that this disclosure is merely illustrative of the presently preferred embodiments of the invention and that no limitations are intended other than as described in the appended claims.

I claim:

1. A catheter assembly comprising:

a flexible elongated catheter body;

a longitudinal fluid supply lumen encompassed within said catheter body; and a longitudinal guidewire lumen formed within said catheter body, said guidewire lumen being separated from said fluid supply lumen by a guidewire conduit wall;

wherein said guidewire conduit wall is adapted to move toward said guidewire lumen, to collapse said guidewire lumen, upon pressurization of said fluid supply lumen.

2. The catheter assembly recited in claim 1, wherein said guidewire conduit wall is formed of a material sufficiently soft, and with a thickness sufficiently thin, to cause said guidewire lumen to collapse when said fluid supply lumen is pressurized to its normal operating pressure.

3. The catheter assembly recited in claim 1, wherein said guidewire conduit wall is formed of a material sufficiently soft, and with a thickness sufficiently thin, to cause said guidewire lumen to collapse when said fluid supply lumen is pressurized to at least about 30 psig.

4. The catheter assembly recited in claim 1, wherein said fluid supply lumen is at least partially defined by a wall of said catheter body.

5. The catheter assembly recited in claim 4, wherein said guidewire conduit wall is formed as a longitudinal partition across said catheter body, thereby partitioning said guidewire lumen from said fluid supply lumen.

6. The catheter assembly recited in claim 4, wherein said guidewire conduit wall is formed as a flexible elongated tube within said catheter body, thereby defining said guidewire lumen substantially surrounded by said fluid supply lumen.

7. The catheter assembly recited in claim 1, wherein said fluid supply lumen is at least partially defined by a fluid supply conduit within said catheter body.

8. The catheter assembly recited in claim 7, wherein said guidewire conduit wall is formed as a longitudinal partition across said fluid supply conduit, thereby partitioning said guidewire lumen from said fluid supply lumen.

9. The catheter assembly recited in claim 7, wherein said guidewire conduit wall is formed as a flexible elongated tube within said fluid supply conduit, thereby defining said guidewire lumen substantially surrounded by said fluid supply lumen.

10. A method for supplying a fluid through a vascular system of a patient, said method comprising:

providing a catheter having a longitudinal fluid supply lumen and longitudinal guidewire lumen therein;

introducing said catheter into a vascular system of a patient over a guidewire, said guidewire passing through said guidewire lumen of said catheter;

withdrawing said guidewire from said guidewire lumen; and pressurizing said fluid supply lumen, thereby moving a guidewire conduit wall into said guidewire lumen, to collapse said guidewire lumen.

11. The method recited in claim 10, wherein:

said fluid supply lumen is at least partially defined by the body of said catheter;

said guidewire conduit wall is formed as a longitudinal partition across said catheter body, thereby partitioning said guidewire lumen from said fluid supply lumen; and said pressurization of said fluid supply lumen flexes said guidewire conduit wall to substantially conform to said catheter body, thereby expanding said fluid supply lumen to occupy substantially the entirety of said catheter body.

12. The method recited in claim 10, wherein:

said fluid supply lumen is at least partially defined by the body of said catheter;

said guidewire conduit wall is formed as a flexible elongated tube within said catheter body, thereby defining said guidewire lumen substantially surrounded by said fluid supply lumen; and said pressurization of said fluid supply lumen collapses said guidewire conduit tube, thereby expanding said fluid supply lumen to occupy substantially the entirety of said catheter body.

13. The method recited in claim 10, wherein:

said fluid supply lumen is at least partially defined by a fluid supply conduit within said catheter body;

said guidewire conduit wall is formed as a longitudinal partition across said fluid supply conduit, thereby partitioning said guidewire lumen from said fluid supply lumen; and said pressurization of said fluid supply lumen flexes said guidewire conduit wall to substantially conform to said fluid supply conduit, thereby expanding said fluid supply lumen to occupy substantially the entirety of said fluid supply conduit.

14. The method recited in claim 10, wherein:

said fluid supply lumen is at least partially defined by a fluid supply conduit within said catheter body;

said guidewire conduit wall is formed as a flexible elongated tube within said fluid supply conduit, thereby defining said guidewire lumen substantially surrounded by said fluid supply lumen; and said pressurization of said fluid supply lumen collapses said guidewire conduit tube, thereby expanding said fluid supply lumen to occupy substantially the entirety of said fluid supply conduit.

* * * * *